United States Patent [19]
Bokros et al.

[11] Patent Number: 5,246,453
[45] Date of Patent: Sep. 21, 1993

[54] PROSTHETIC HEART VALVE

[75] Inventors: Jack C. Bokros; Michael R. Emken, both of Austin; Axel D. Haubold, Liberty Hill; T. Scott Peters, Georgetown; Jonathan C. Stupka, Austin, all of Tex.

[73] Assignee: Onx, Inc., Austin, Tex.

[21] Appl. No.: 919,285

[22] Filed: Jul. 24, 1992

Related U.S. Application Data

[62] Division of Ser. No. 674,871, Mar. 25, 1991, Pat. No. 5,152,785.

[51] Int. Cl.⁵ .......................... A61F 2/24; F16K 15/00
[52] U.S. Cl. .......................................... 623/2; 137/527
[58] Field of Search .................. 623/2, 3, 1; 137/521, 137/527

[56] References Cited

U.S. PATENT DOCUMENTS

| | | | |
|---|---|---|---|
| 4,308,624 | 1/1982 | Klawitter | 3/1.5 |
| 4,328,592 | 5/1982 | Klawitter | 3/1.5 |
| 4,425,670 | 1/1984 | Figuera | 3/1.5 |
| 4,443,894 | 4/1984 | Klawitter | 3/1.5 |
| 4,872,875 | 10/1989 | Hwang | 623/2 |
| 5,116,366 | 5/1992 | Hwang | 623/2 |

Primary Examiner—Randall L. Green
Assistant Examiner—Dinh X. Nguyen
Attorney, Agent, or Firm—Fitch, Even, Tabin & Flannery

[57] ABSTRACT

Bi-leaflet and single occluder heart valves have improved pivot arrangements that create quick valve response to flow reversal and minimize impact. Valve members or occluders, which have curved inflow and outflow surfaces, are slidably and pivotally mounted in a heart valve body and can be aligned precisely parallel to blood flow in the open position. Lugs on the valve members engage surfaces on projections extending radially inward from flat wall sections in the valve body sidewall, and the shape and relationship of these interengaging surfaces provide prompt initial rotation, low wear and reduced impact upon closing. Laterally directed ears engage the valve body arcuate sidewall and assist in defining the path of closing movement.

20 Claims, 5 Drawing Sheets

PROSTHETIC HEART VALVE

This application is a division of our application Ser. No. 07/674,871, filed Mar. 25, 1991, now U.S. Pat. No. 5,152,785.

BACKGROUND OF THE INVENTION

The present invention pertains to heart valve prostheses and in particular, to prosthetic heart valves having valve members which both pivot and translate, including single occluder and bi-leaflet valves.

DESCRIPTION OF THE PRIOR ART

Various types of heart valve prostheses have been developed which operate hemodynamically as a result of the pumping action of the heart. Such heart valves include valves having single occluders which pivot along an eccentric axis (or both pivot and translate), to open and close the blood flow passageway, such as those described in U.S. Pat. Nos. 3,546,711, 4,011,601, 4,425,670 and 4,725,275, and also include bi-leaflet heart valves, such as those described in U.S. Pat. Nos. 4,078,268, 4,159,543 and 4,535,484. The above-mentioned patents illustrate various different arrangements for pivotally connecting valve members (i.e. occluders) to valve bodies and disclose occluders of a variety of shapes. However, most of these designs have never become commercial because of some shortcoming, and the need continues for improved prosthetic heart valves for permanent implantation into the human heart.

In its open position, a prosthetic valve should provide a passageway which is large and which has good flow characteristics so that blood flows freely therethrough without adverse boundary layer separation and with a minimum of drag. The heart valve should be responsive to blood flow to open quickly during the pumping stroke of the heart and to close quickly when the heart relaxes, to prevent any substantial regurgitation of the blood. The opening and closing of the valve should be sufficiently soft so that the patient is not disturbed by the sounds produced. The heart valve must, of course, be made of materials that are biocompatible and thromboresistant, and in this regard, it is important that all surfaces be well washed by blood to prevent stagnation which might lead to eventual clotting. Furthermore, the action of the valve should be such that it does not cause hemolysis (damaging of blood cells), and of course, the heart valve should be constructed to withstand countless openings and closings and should not be prone to the creation of particular regions of wear.

SUMMARY OF THE INVENTION

The present invention provides heart valves having the aforementioned desirable characteristics wherein the valve member or occluders are designed to promptly open and close in response to reversal of the flow of blood, while providing a particularly low-resistance flow path in the open position, thereby resulting in excellent operating characteristics. The foregoing characteristics are obtained in certain particularly preferred versions where the occluder or occluders assume an orientation that is parallel, or nearly parallel, to the direction of blood flow in the open position, thus allowing particularly efficient blood flow therethrough in a downstream direction.

The valves each have a generally annular valve body formed with an interior sidewall, which defines a central passageway therethrough for the passage of blood in a downstream direction. One or more occluders mounted in the valve body to alternately permit the flow of blood therethrough in a downstream direction and block blood flow in the reverse direction utilizing a pivot arrangement which includes projections extending inward from the valve body sidewall that coact with lugs formed on the occluder(s). These projections are preferably formed with first and second flat surfaces which are oriented to respectively lie in juxtaposition with complementary occluder surfaces which may be on the lugs, in both the open and closed positions.

In another aspect, each of the projections is formed with at least one flat surface that is parallel to the centerline of the flow passageway through the valve body. In this instance, such surfaces are positioned so that, when an occluder is in the open position, this flat surface is in juxtaposition with a complementary flat surface portion of the occluder whereby the downstream flow of blood through the valve body finds the occluder disposed substantially parallel to blood flow, thus providing minimum resistance to blood flow; the reverse flow of blood in an upstream direction, however, causes upstream displacement such that the lugs engage the projections and cause the occluder to promptly begin to pivot toward its closed position.

In a further aspect, the design can be such that the center of rotation of the pivot (CRP) is initially spaced beyond the outflow surface of the occluder, to provide for a high initial pivot moment. However, it then shifts to a location generally near the inflow surface, reducing the pivot moment and providing for a soft final closing movement.

In still another aspect, the pivot design in a bi-leaflet valve can be such that, at about the instant of closing, when there is first contact between the arcuate downstream edge of a leaflet and the valve body sidewall, all of the forces acting upon the leaflet (when viewed in a 2-dimensional projection) intersect near a common point. As a result, the pressure load is most efficiently carried (i.e., the load on the upstream pivot is a minimum for any given pressure acting upon the downstream surface of the leaflet), and thus wear at this point is also minimized. Moreover, by offsetting the surface slightly, i.e., up to about 10°, there can be a small resultant force continuing to cause the occluders to pivot in a direction so as to assure that the mating edges of the leaflets abut.

BRIEF DESCRIPTION OF THE DRAWINGS

FIG. 19 is a cross-sectional view similar to FIG. 9 showing still another alternative embodiment of a heart valve having various features of the invention.

DETAILED DESCRIPTION OF THE PREFERRED EMBODIMENTS

FIGS. 1-9 show one preferred embodiment of a heart valve prosthesis constructed according to principles of the present invention. The heart valve, generally designated as 10, is of a bi-leaflet construction, but it will be readily apparent to one ordinarily skilled in the art that the principles of the present invention can be applied to a prosthetic heart valve of single occluder construction.

Both versions of heart valves have numerous advantages as will be described herein; for example, such heart valves will provide improved flow characteristics when the valve is in a fully open position. They substantially reduce boundary layer separation at major surfaces of the occluders, particularly when the occluders are aligned substantially parallel to the valve centerline in the open position, thus minimizing drag, while also providing good wash characteristics so as to prevent stagnation. In addition, such heart valves provide a rapid response upon opening and closing, with a relatively small impact when the occluders contact the valve body so as to reduce hemolysis or like injury to blood cells flowing through the valve, and regions of potentially substantial wear are also eliminated.

Referring initially to FIGS. 1-9, heart valve 10 includes a generally annular valve body 12 which carries a pair of pivoting occluders or leaflets 14 that open and close to allow the flow of blood in the downstream direction of arrows 18 and to prevent any substantial backflow. Blood flows through passageway 16 which is defined by a generally cylindrical interior surface or sidewall 20 of valve body 12. The otherwise cylindrical sidewall surface 20 is interrupted by a pair of diametrically opposed, flat wall sections 24. In the general region of each of these flat wall sections are a first centrally located projection 26 and a pair of flanking second projections 28 which coact to define the generally rotative movement of the leaflets 14 when the leaflets move from the fully open position to the closed position, and vice versa.

Figure 1:
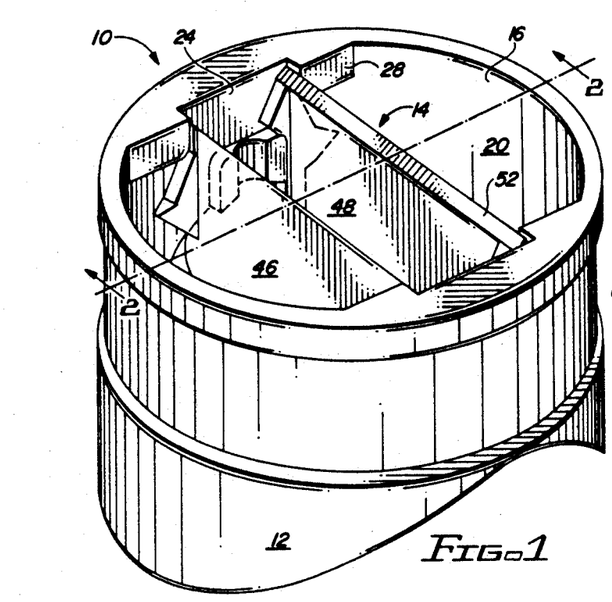
FIG. 1 is a perspective view of a bi-leaflet heart valve embodying various features of the present invention, shown in its open position.

As seen in FIG. 1, these sets of projections 26 and 28, which are positioned at diametrically opposed locations on the valve body, extend generally perpendicularly from the surface of the flat wall sections 24. The central projection 26 has two oppositely facing flat surfaces 30a and 30b, each of which is substantially parallel to the valve centerline, and a second surface 32 which is preferably transverse, e.g. oriented approximately perpendicular to the valve centerline. The edges between these three surfaces are preferably faceted or rounded (see FIG. 2). In this embodiment, each of the second projections 28 has a flat surface 34 which is oriented substantially parallel to the direction of blood flow, i.e. the valve centerline, and also has a second, transverse (e.g. generally perpendicular) surface 36; these surfaces intersect at what is termed a downstream edge 38 of the projection 28 (see FIG. 7) which may be faceted or rounded as shown. The middle section 40 of the central projection 26 is preferably concave with respect to the centerline of the valve body 12 so as to minimize the area impeding the flow of blood through the passageway 16. The second projections 28 taper in thickness (see FIG. 3) so as to blend into the sidewall 20 of the valve body at their outer extremities, i.e. having front surfaces 42 which are flat and generally parallel to the flat wall section 24 of the valve body.

Figure 5:
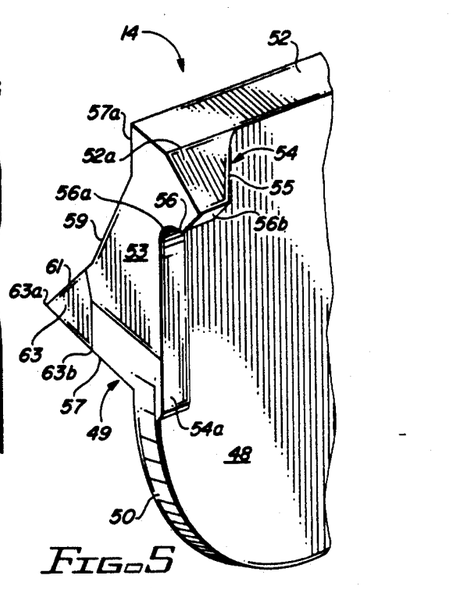
FIG. 5 is a fragmentary bottom perspective view of the leaflet shown in FIG. 4.
Figure 9:
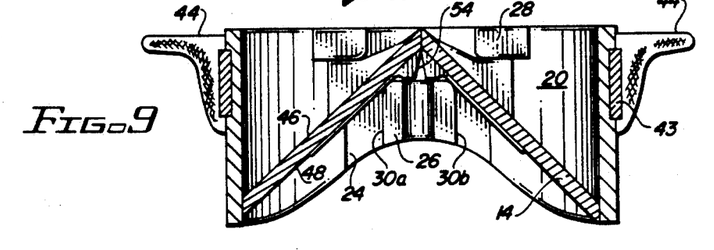
FIG. 9 is a cross-sectional view of the heart valve of FIG. 1 in the closed position.

The outer surface of the valve body 12 is preferably grooved to receive a metal stiffening ring 43 which in turn supports a sewing ring 44 (see FIGS. 5 and 9). The sewing ring 44 can be of a conventional design as well known in this art.

Figure 2:
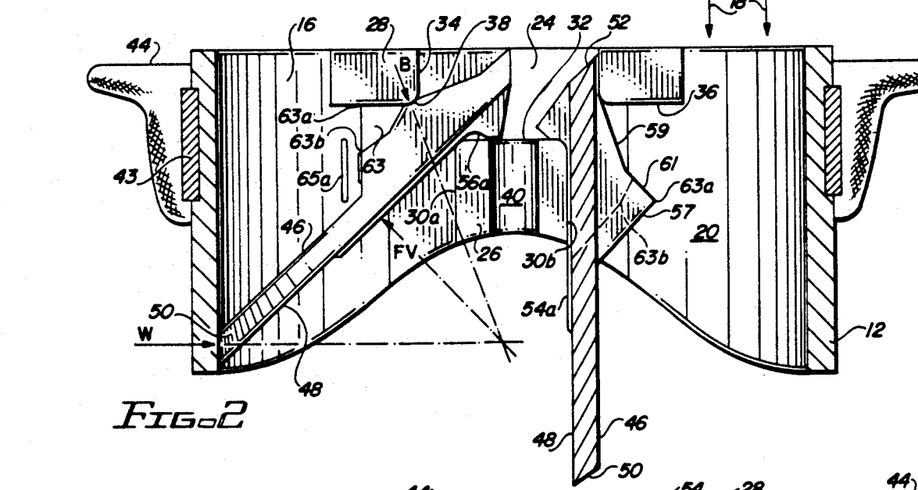
FIG. 2 is an enlarged cross-sectional view of the heart valve taken along the line 2—2 of FIG. 1, showing the valve with the right hand leaflet in its open position and with the left hand leaflet shown in elevation and in its closed position.

Referring now to FIG. 2, the leaflets 14 each have an upstream-facing or inflow surface 46 and an opposed downstream-facing or outflow surface 48 (with reference to the leaflets when positioned in the closed position). The leaflets can be essentially flat and thus of substantially uniform cross-sectional thickness, except for side sections 49 located along each lateral edge where lugs are formed which coact with the projections 26 and 28 to define the opening and closing movements of the leaflets. Alternatively, the leaflets can have considerably different shapes, such as having a generally cylindrically shaped main body section, as described hereinafter with respect to FIGS. 10-12.

Figure 8:
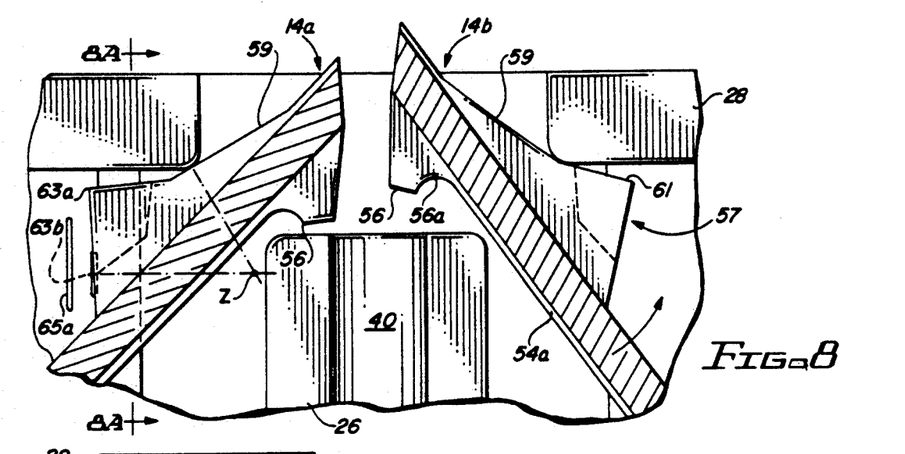
FIG. 8 is an enlarged, fragmentary, cross-sectional view similar to FIG. 7 again showing both leaflets in slightly different second intermediate position in their movement toward the closed position.
Figure 8A:
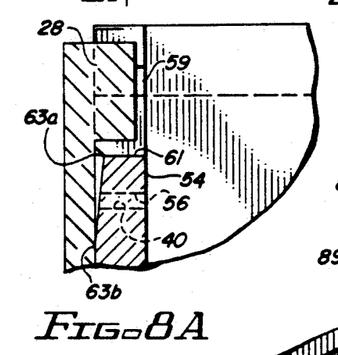
FIG. 8A is a fragmentary sectional view taken along line 8A—8A of FIG. 8.

The leaflets 14 each have a major arcuate edge surface 50, which is located at the downstream edge of the leaflet in its open position, and a minor mating edge surface 52 which is located at the opposite, upstream edge of the leaflet (again, assuming a leaflet in an open position). The arcuate edge surface 50 preferably has a configuration to abut and seat against the cylindrical sidewall 20 of the valve body in the closed position. The minor edge surface 52 is preferably of a configuration so as to mate with the corresponding mating surface to the opposing leaflet, and this minor surface 52 is oriented at an angle such that the two mating edge surfaces of the leaflets 14 abut while extending across the diameter of the valve passageway when in the closed position, as is well known in the art of bi-leaflet valves. As seen in FIGS. 8 and 9, each side section 49 has a lower beveled section 52a that provides clearance between the two leaflets during their closing and their initial opening movements.

Figures 3, 4, 6:
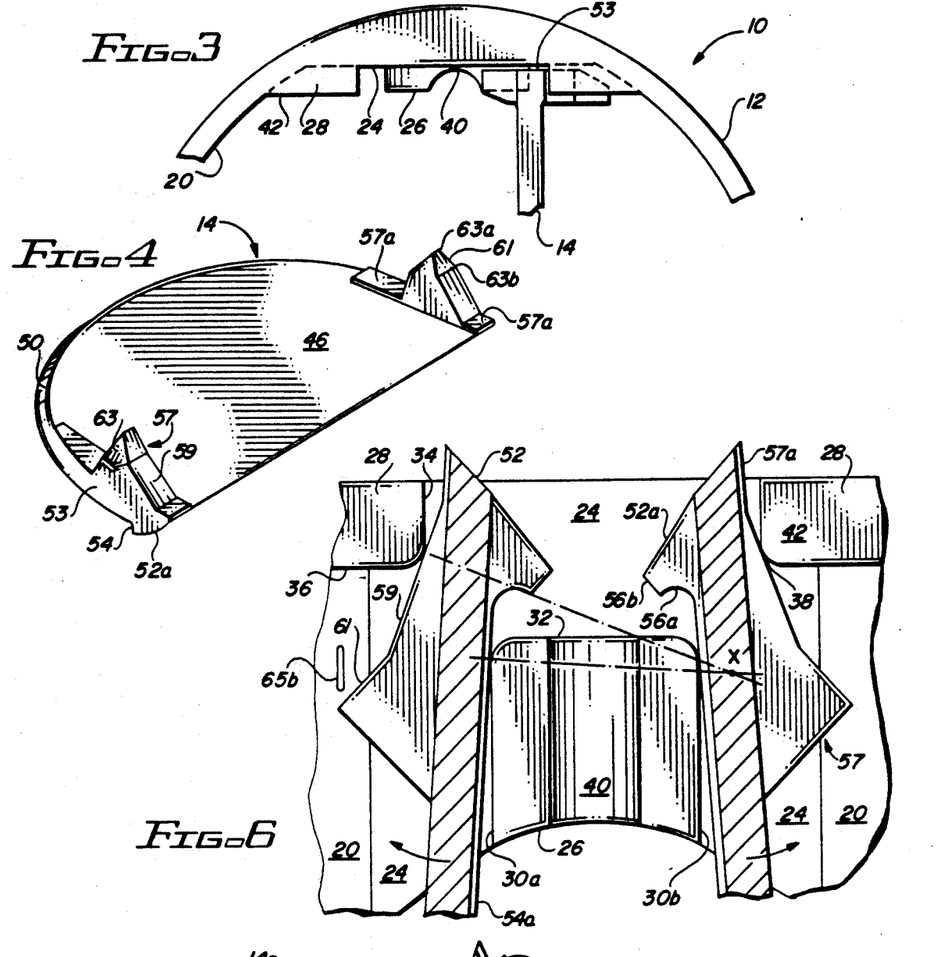
FIG. 3 is a partial plan view of the bi-leaflet heart valve shown in FIG. 1 with one leaflet removed and one in its open position.
FIG. 4 is a perspective view of a leaflet from the valve shown in FIG. 1.
FIG. 6 is an enlarged, fragmentary, cross-sectional view similar to FIG. 2 showing the leaflets shortly after they have begun to move toward the closed position.

Referring to FIGS. 4 and 5, the leaflets 14 each include a pair of opposed, lateral surfaces 53 which are interposed between the major arcuate surface 50 and the minor mating surface 52. These lateral surfaces 53 of the leaflets are preferably flat, and the leaflets are proportioned so as to provide minimal clearance adjacent the flat wall sections 24 of the valve body 12 (see FIG. 3), so as to enable the leaflets 14 to pivot, with these lateral edge surfaces 53 moving adjacent to the flat wall sections 24, one of which is usually serving as a bearing surface.

Referring to FIG. 5, extending from the outflow surface 48 of each leaflet 14 in each side section 49 is an integral first or opening lug 54. These lugs 54 extend in a direction toward the centerline (in the open position) and have upstream surfaces 52a that are beveled, i.e. slightly angularly offset from the minor edge surface 52; this offset prevents their interference with each other during closing and opening as indicated above. The lugs 54 have downstream surfaces 56 oriented to engage and lie in juxtaposition with the transverse surface 32 of the central projection 26 in the closed position. These surfaces 56 are preferably oriented at an angle of between about 135° and about 150° to the flat outflow surface 48, viz. at an angle of between about 30° and about 45° to the centerline plane in the open position. This downstream surface 56 may be formed with a recess 56a which accommodates the rounded edge of the projection 26, as seen in FIG. 2, when in the open position and prevents the leaflet from escaping downstream. As shown hereinafter, the edge of the downstream projection 26 could be faceted. The radially inward-facing surface 55 of each lug 52 is preferably tapered outward toward its base so as to assure the lug has adequate structural strength, as seen in FIG. 5.

Second or closing lugs 57 are also preferably formed in the side sections 49 as an integral part of the leaflets 14 and protrude from the inflow surface 46 of each occluder, with one such lug being located generally along each lateral edge of the leaflet. The second lugs 57 each have a front camming surface 59 which is arranged so as to lie at a desired acute angle to the plane of the flat surface of the major body portion of the occluder, and can have, as best seen in the right hand leaflet of FIG. 2, an extension 57a which is oriented parallel to the centerline of the valve body when in the open position. These lugs 57 which extend in an upstream direction with the leaflets in the closed position are sometimes referred to as the upstream lugs. The front camming surfaces are oriented at an angle of between about 5° and about 35°, preferably about 30°, to the centerline plane in the open position. The lug 57 also has a rear angular surface 61 which is oriented at an angle of between about 30° and about 45° to the centerline plane in the open position so as to lie generally in juxtaposition with the transverse surface 36 of the projections 28 when the leaflets are in the closed position.

The front camming surface 59 may extend to and meet with the rear surface 61 as shown in the embodiments in FIGS. 1 through 9, or there may be an intermediate surface separating the two or a slight recess at the point of junction, as shown in some of the alternative embodiments described hereinafter.

The radially outer lateral surfaces of the lugs 57 are chamfered near their upper ends to provide a small generally triangular surface 63 on each that generally provides clearance for the lug when it rotates in the region beyond the flat wall 24 of the valve body 12, as best seen in the right hand portion of FIG. 2. The chamfer is precisely located (see left hand leaflet of FIG. 2) so as to create an upper bearing point or ear 63a which engages the curved sidewall of the valve body during an intermediate portion of the closing movement (see FIG. 7) and a lower bearing point or ear 63b which engages the curved sidewall during the later stages of the closing movement of the leaflets. These ears assist in guiding the rotation of the leaflets in the closing movement after the leaflet has lost sliding contact with the downstream projection 26 (which contact is illustrated in FIG. 6); the ears 63a and 63b are best seen in FIG. 5. There are two lines of contact, or rub lines 65a and b that extend generally parallel to the centerline of the valve body at the locations where there can be contact, respectively, between the upper ears 63a and the lower ears 63b with the valve body sidewall, as best seen perhaps in FIGS. 8 and 8A. The sizing of the leaflets is such that contact of the ears on opposite lateral sides of a leaflet and the respective rub lines will not occur simultaneously. This contact between the lower ear 63b and the curved sidewall 20 of the valve body, which creates the rub line 65b, is shown in the fragmentary cross-sectional view 8A.

In addition to these angular surfaces of the lugs, both lugs can include elongated thickening sections 54a and 57a, respectively, that extend parallel to the inflow and outflow surfaces along the leaflet lateral edges 53. These strengthen the lateral regions or side sections 49 of the leaflets where engagement occurs as a result of the pivoting arrangement, while allowing the major body portion of the leaflets 14 to remain relatively thin so it will provide less resistance to blood flow.

The leaflets 14 are installed in the valve body 12 by squeezing the body at diametrically opposed locations, i.e. those where the valve body is cut by the reference line 2—2 in FIG. 1. This causes the diametrically opposed flat wall sections 24 to further separate, thus allowing the leaflets 14 to be fitted into the passageway 16 of the valve body. The side sections 49 at the lateral edge regions of the leaflets containing the first lugs 54 and second lugs 57 are received between the projections 26 and the projections 28 of the valve body. When the squeezing force is removed, the valve body 12 returns to its original configuration, leaving the desired minimal clearance between the flat wall sections 24 of the valve body 12 and the lateral edge surfaces 53 of the leaflets as discussed above. The locations of the projections 26 and the projections 28 is such that the leaflets may initially translate slightly but then quickly begin to rotate in traveling from the open to the closed position, while the leaflets always are maintained in functional operating attitudes. This is discussed further below in relation to the operation of the valve.

As will be appreciated by those skilled in the art, the leaflets 14 and heart valve body 12 have relatively simple configurations which are easy to machine; they also provide improved economics of fabrication in that tolerances of the heart valve components are easily maintained. The leaflets are slidably-pivotally mounted for travel between closed and open positions, and it is generally preferred that the leaflets 14 are oriented parallel to the valve centerline in the open position to create minimal turbulence and flow separation. The illustrated design allows such a precisely parallel orientation to be achieved while still assuring that the closing movements of the leaflets begin very rapidly as flow reversal occurs. It also allows for the leaflets to be made just slightly longer in length than required to abut each other so that, even taking manufacturing tolerances into consideration, there cannot be a significant leak between the mating edges 52. Moreover, the resultant torque that is driving each leaflet 14 is initially relatively high, but as the leaflet nears its closing end point, it is reduced because of the shortening of the closing moment arm through which the main force acts, which shortening is an inherent feature of the pivot arrangement design and occurs throughout the closing movement. This reduces noise and leaflet impact and wear, and it significantly lowers the tendency for the leaflets to bounce back upon reaching the closing end points.

Figure 7:
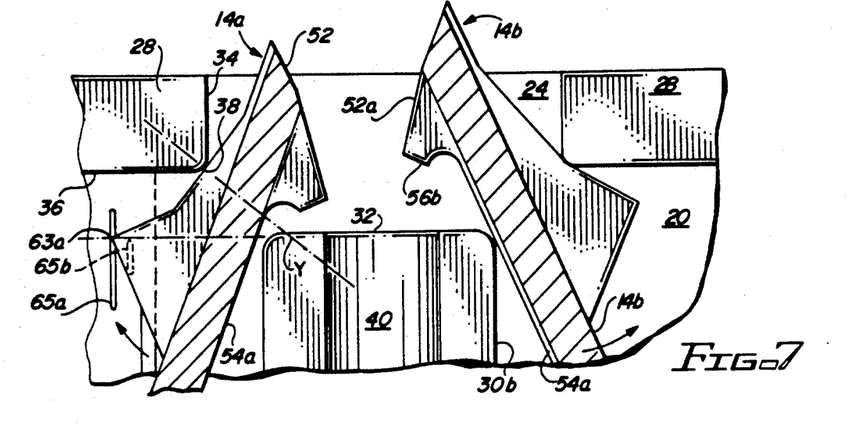
FIG. 7 is an enlarged, fragmentary, cross-sectional view similar to FIG. 6 showing both leaflets in slightly different intermediate positions in their movement toward the closed position.

For illustration and comparison purposes, FIG. 2 shows the valve 10 with the left-hand leaflet in the closed position and with the right hand leaflet in the full open position, although it should be understood that such an orientation would never occur as the two leaflets 14 move substantially simultaneously with each other. In this respect, attention is directed to FIGS. 6 and 9 of the drawings wherein representative movement of the leaflets from the open to the closed position is illustrated. FIGS. 7 and 8 show intermediate position with the RH and LH leaflets having different orientations for purposes of explanation.

The fully open leaflet position is shown on the right hand side of FIG. 2 wherein the recess 56a of the first lug 54 is in contact with the rounded edge between the surfaces 30 and 32 of the first or central projection 26. The flat extension portions 54a of the first lugs (along the outflow surfaces) are in contact with the surface 30b of the projections 26 and thus lie substantially parallel to the centerline. The thin parallel extensions 57a of the lug 57 are similarly in contact with and lie in juxtaposition to the surface 34 of the projection 28 (which surface is also parallel to the centerline). Thus, in the open position, the major body portion of the leaflet extends substantially parallel to the valve centerline, thus providing minimum obstruction to the downstream flow of blood.

Upon the reversal of blood flow as a result of the contraction of the heart, the backflow of blood creates a drag on the surfaces of the leaflet, displacing it upwardly (with reference to FIGS. 2 and 6). A brief initial movement may be one of pure translation, i.e. all points on the body are simultaneously moving in the same direction at the same velocity, with the amount of translation being dependent upon the location of the upstream end of the camming surface 59 and the amount of tolerance in the spacing between projections 26 and 28. The presence of the front camming surface 59 causes the leaflet 14 to substantially immediately begin to rotate (see FIG. 6) as it continues to slide upward, maintaining contact between the camming surfaces 59 and the curved edges 38 of the upstream projections 28. During the first phase of closing movement, contact is likely maintained between the extension regions 54a of the first lug and the curved upstream edges of the center projection 26; however, this contact depends upon the spacing (in the generally radial direction) between the central projections 26 and the flanking projections 28 and the dynamic conditions within the bloodstream. This prompt rotation continues to expose the outflow surface 48 of the leaflet to more and more of the full force of the backflowing stream of blood, thereby amplifying the rotative force vector being applied against each leaflet.

Illustrated in FIG. 7 are positions where continued sliding-pivotal movement has occurred and where the contact of the left hand leaflet 14a with the downstream projection 26 has ended so that further movement is being defined by the camming surface 59 and the upper ears 63a, which have moved into engagement with the curved sidewall 20 along the rub line 65a the upper end of which is approached. Once the end is reached, the next movement of the leaflet will be defined by the camming surfaces 59 and the lower ears 63b which will travel upward along the shorter rub lines 65b (which as shown in FIGS. 6 and 7 are located slightly nearer the valve centerline when projected onto a plane perpendicular to the pivot axis of the leaflet). When the lower ears 63b have nearly reached the upper ends of the rub lines 65b, the travel of the camming surface 59 along the downstream projection edge 38 is such that the junction between the front and rear surfaces 59, 61 has nearly been reached (as illustrated generally in FIG. 8 with respect to the left hand leaflet).

If external forces upon the patient or dynamic forces within the bloodstream at the valve are such, an intermediate position such as that illustrated by the right hand leaflet in FIG. 7 may be reached where the sliding-pivoting movement has been such that the junction between the front camming surface 59 and the rear surface 61 has reached the downstream edge 38 of the projection 28 without any contact of either of the ears 63a,b with the rub lines 65a,b. Thereafter final movement is generally only one of rotation about a fixed pivot point. As shown in FIG. 8, as this pure rotation of the right hand leaflet 14b continues, the primary function of the upstream projection 28 is one of pivotal support for the leaflet at the junction between front camming surface 59 and the rear surface 61, and contact between the lug extensions 54a and the central projections 26 has terminated at this stage of the movement. By comparing the right hand leaflets 14b in FIGS. 7 and 8, it can be seen that the outflow surface 48 of the leaflet moves away from the central projection 26 as pure rotation begins toward the further intermediate location being shown in FIG. 8. Thus, final movement from the orientation of FIG. 7 is generally that of movement about a fixed pivot.

It is anticipated that leaflet movement will generally follow the path of the left hand leaflets 14a in FIGS. 7 and 8, with the locations of the ears 63a and 63b playing a part in defining the precise CRP (center of rotation of pivot) for each leaflet as the closing movement continues. The CRP is located by drawing perpendiculars to the leaflet surface at each point of contact to see where they intersect. The left hand leaflet 14a in FIG. 8 should continue to travel so that the lower ear 63b reaches the top of the rub line 65b at the same time as the downstream end of the camming surface 59 reaches the edge 38 of the projection 28. However, depending upon the extent of the chamfer which creates the triangular surface 63, contact between the ear 63a and the sidewall might cease as the leaflets are in their final approach to the fully closed position, which is still acceptable.

The last phase of the movement occurs when the arcuate downstream edge 50 (see FIG. 2) of the leaflet makes contact with the interior sidewall of the valve body. Whichever leaflet happens to close first, i.e. its major arcuate edge is the first to contact the sidewall 20, its mating edge surface 52 may extend past the centerline by 1 or 2 thousandths of an inch, if the manufacturing tolerance is such that it was slightly oversized; however, such a situation will be accommodated when the second of the two leaflets reaches the fully closed position, thereby positively assuring that there is contact between the primary flat facing surfaces of the mating edges 52 so as to insure against any substantial amount of leakage that might potentially result from a mismatch of valve components should both coincidentally happen to have been sized at opposite ends of manufacturing tolerances—such as is possible in other mechanical heart valves having different pivot arrangements. FIG. 9 shows the leaflets in the closed position, wherein they are preferably oriented with their flat main body surfaces 46, 48 at an angle of between about 30° and about 45° to the centerline plane. In this position, the surfaces 56 of the lugs 54 are spaced slightly above, but in juxtaposition with, the upstream surfaces 32 of the central projections 26.

When the next cycle occurs so that there is again a flow of blood in the normal downstream direction through the valve, the force of the blood on the inflow surfaces 46 of the leaflets 14 causes immediate displacement slightly downward until the surface 56b of the first or opening lug 54 contacts the upstream-facing surface 32 of the center projection 26. This causes pivoting of the leaflets in the opening direction to occur, with such pivoting being primarily guided by the engagement between the surfaces 56 and 54a of the opening lugs 54 with the center projection 26 although there may be some slight, short engagement between the ears 63a and b and the valve body sidewall. Such rotation continues until the fully open position is reached with the leaflets 14 in a substantially parallel position with respect to the valve centerline. In this position, the rounded upstream edges of the projection 26 interengage of the lugs 54 engage the transverse surface 32. The projection side surfaces 30 are also in juxtaposition with the flat surfaces of the thin lug extensions 54a, and the shorter extensions 57a of the upstream lugs 57 lie in juxtaposition with the side surfaces 34 of the upstream projections 28, thus assuring stable support in this open orientation until the next reversal of blood flow.

A particularly advantageous pivot arrangement is created by the use of projections 26, 28 spaced apart in this manner (which extend from the two diametrically opposed flat sidewall sections 24 of the valve body) in conjunction with the oppositely extending lugs 54, 57 located along the lateral edges of each leaflet. There is a prompt and rapid rotation of the leaflets 14 about a center of rotation of pivot (CRP) that initially is spaced a significant distance, preferably at least a distance equal to one-half the radius of the valve passageway, beyond the outflow surface of the leaflet when closing movement first begins. For example, in FIG. 6, which illustrates the position after a slight amount of rotation has actually taken place, the CRP for the left hand leaflet is at point X a substantial distance on the opposite side of the centerline plane of the valve, i.e. the plane which contains the centerline of the passageway and is parallel to the axes of rotation of the valve members; most preferably this distance is equal to at least half the radius of the passageway. As a result, there is a very large initial effective torque which drives the leaflet in its rotational movement, achieving a prompt response in moving the leaflets toward the closed position and minimizing regurgitation of blood. There is also a similar, large moment arm which contributes to achieving prompt initial rotational movement of the leaflets moving to the open position. However, a further significant advantage is found in this pivot construction because the CRP, during closing, moves from its initial location, which is not only well beyond the outflow surface of the leaflet but also well beyond the centerline plane for a bi-leaflet valve (thereby encouraging prompt rotational movement as a result of the large moment arm), to a location generally close to the outflow surface 48 or even beyond the inflow surface 46 of the leaflet when the leaflets near the end of closing rotation. The result of this change in CRP location is a lessening of the rotational moment arm and a consequent softening of the final impact of the leaflet against the valve sidewall, thereby reducing both noise and wear.

The term CRP is used to describe the theoretical instantaneous pivot center about which rotation of the leaflet is occurring at any instant in its movement from the open position to the closed position, and vice versa. Where there is contact at two locations along each lateral edge region of the leaflet, i.e., with the projection 28 and with either the projection 26 or the valve body sidewall at one of the rub lines 65, the CRP is determined by constructing perpendiculars to the respective surfaces of the leaflet at the precise points where contact occurs and then determining the point where those perpendiculars cross. The CRP is shown for the left hand leaflet in FIG. 6 as point X, in FIG. 7 as point Y and in FIG. 8 as point Z, with the latter two points being close to the outflow surface 48. On the other hand, when the leaflets shift to the locations shown for the right hand leaflets 14b in FIGS. 7 and 8, the CRP is thereafter located at the junction between the camming surface 59 and the near surface 61, which is slightly beyond the inflow surface 46.

Comparison will show that there is initially a very large rotational moment arm because the CRP was initially spaced a relatively long distance from the point on the outflow surface of the leaflet which corresponds to the point at which a single vector can be applied that will be equivalent to the sum of all of the closing (or opening) forces upon the leaflet. Such a point can be computed to be generally located close to the geographic center of the outflow surface 48 in the late stages of closing, but in the early stage of lift upon a flat plate such as this, the composite force vector (FV) is computed to act through a central point located about 25% of the length of the leaflet from the edge 50 which is the leading edge with respect to the backflow of blood. It should be apparent that this moment arm, defined by the distance between this point and the CRP, has been considerably shortened in FIGS. 7 and 8. Moreover, in FIG. 8, the CRP for the right hand leaflet 14b is at or very near the intersection between the front camming surface 59 and the rear surface 61 of the closing lug 57. The result of the shortening of the distance between the CRP and the point at which the composite force vector is being applied, as a result of migration of the CRP from a point far beyond the outflow surface (in the direction away from the occluder) to a point near the surface of the leaflet, is particularly advantageous. It results in a reduction in the closing impact of the leaflet and also in a reduction of the amount of any final sliding movement of the leaflet in reaching the closed position at a time when the pressure differential across the leaflet is highest and thus would contribute the greatest to wear.

In addition, as shown with the LH leaflet in FIG. 2, at the point of closure, the closing force is represented by the composite closing force vector FV, and the opposite and equal forces are the force W (at which the arcuate edge 50 of the leaflet bears against the cylindrical sidewall of the valve body) and the force vector B, which is located at the point of engagement between the camming surface 59 and the downstream edge of the projection 28. In the illustrated embodiment, the orientation of the camming surface 59 is such that the force vector B is applied along a line so that these three forces meet at about a point Q so there is no final closing torque, which as mentioned above, reduces wear.

Figures 10, 12:
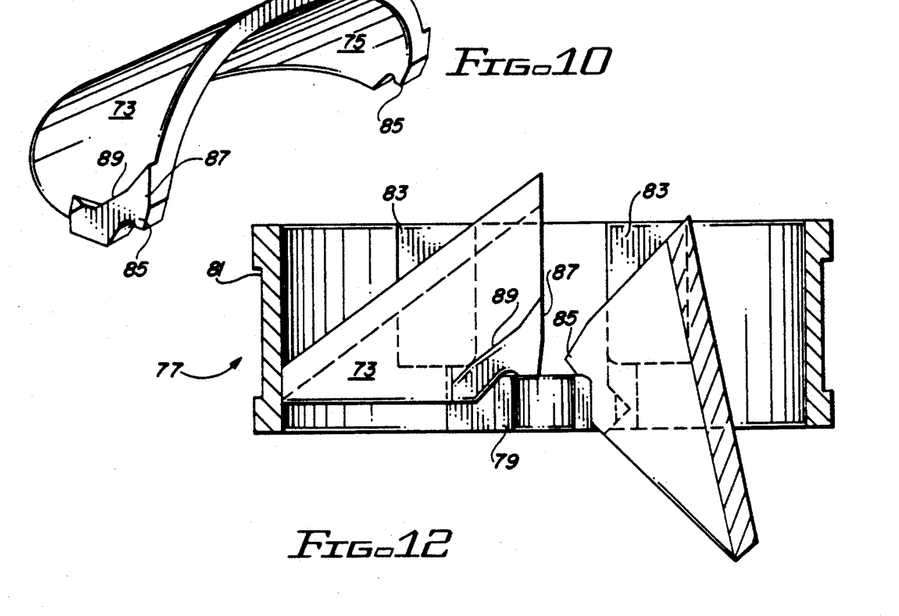
FIG. 10 is a perspective view showing an alternative embodiment of a leaflet which is curved that might be employed in a valve of the general type shown in FIG. 1.
FIG. 12 is a cross-sectional view of a valve incorporating a pair of the leaflets shown in FIGS. 10 and 11, which view is generally similar to FIG. 2, with the left-hand leaflet shown in elevation.
Figure 11:
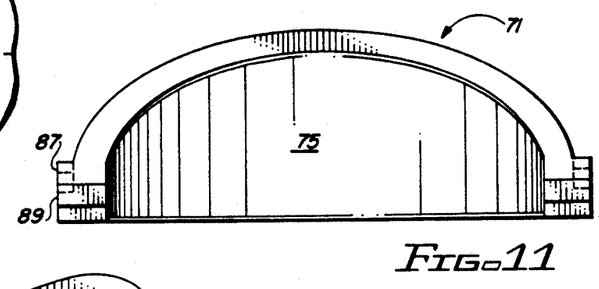
FIG. 11 is a front view of the leaflet of FIG. 10.

Shown in FIGS. 10, 11 and 12 is an alternative embodiment of a curved leaflet 71 which has a convex curved inflow surface 73 and a concave curved outflow surface 75 that form its main body portion which, instead of being substantially a flat plate as in the case of the leaflets 14 hereinbefore described, is a section of a tube or hollow cylinder of elliptical or oval cross section. As a result, in the open position, a heart valve 77 using two of these leaflets 71 (see FIG. 12) has an enlarged central flow channel section compared to the valve 10 where two leaflets 14 having the flat body sections are employed. However, the main body of each leaflet is of substantially uniform thickness and can be oriented substantially parallel to the direction of blood flow to again present minimal resistance.

From the standpoint of guiding the movement of the leaflets 71 between the open and closed positions, a valve body 81, which is of essentially the same design as the valve body 12, is employed. Because of the relative location of the pivot arrangement to the main body portion of the curved leaflets 71, a central downstream projection 79 is located further downstream from the upstream edge of the valve body 81 resulting in upstream projections 83 which are elongated although they could be shortened or chamfered at their upper ends. The valve body 81, as shown in FIG. 12 could be shorter in height in comparison to FIG. 2 because the downstream arcuate edge surface abuts the valve sidewall at an axial location near the leaflet pivot axes. The side sections of the curved leaflets 71 are shaped to have lugs 85 and 87 which have functional and camming surfaces 89 that are substantially the same as those described hereinbefore with respect to the leaflets 14, and as a result, it will be apparent that the rotational movement of the curved leaflets 71 will be substantially the same as that hereinbefore described for the leaflets 14 because the side sections have such similar lugs 85, 87.

Consequently, it can be seen that the various advantages of the valve construction hereinbefore described are independent of the particular shape of the main body of the leaflets; however, it should be apparent that the main body portions of the leaflets 71, although curved in profile, are rectilinear, i.e. made up of a locus of straight lines which are parallel to one another and which can extend parallel to the centerline of the valve in the open position. Thus, these two-dimensionally curved leaflets 71 having a main body portion that is a section of an elliptical or oval cross section tube (the axis of which tube is parallel to the valve body centerline in the open position) provide minimal resistance to flow of blood and also minimize flow separation.

Figure 13:
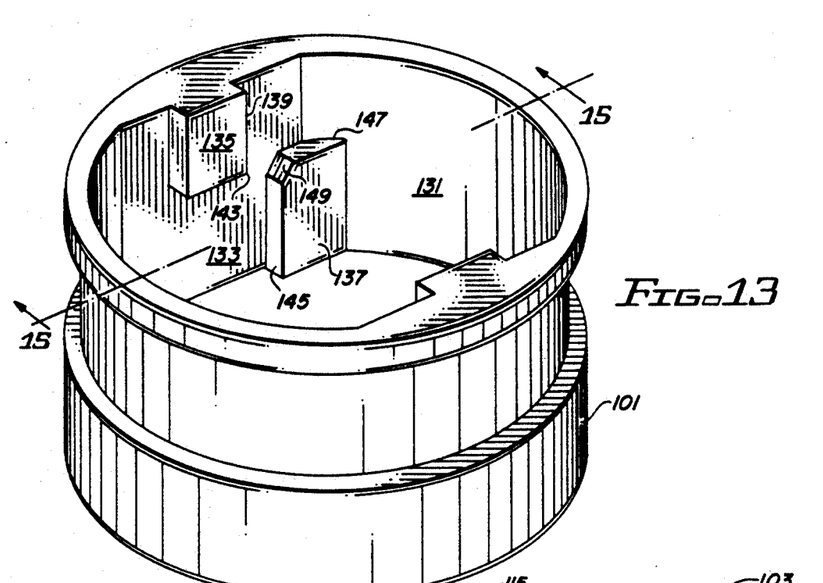
FIG. 13 is a perspective view, generally similar to FIG. 1, showing a valve body designed for use with a single occluder (without the occluder installed)

Shown in FIGS. 13-16 is a single occluder version of a heart valve 99 embodying various features of the invention which has many of the advantages that are found in the bi-leaflet versions described hereinbefore. FIG. 13 shows a valve body 101 designed to accommodate a single occluder or valve member 103 that will slidably-pivotally move from an open to a closed position and vice versa. The valve member 103, shown in FIG. 14, has a flat main body section 105 in the region of the pivots and has a slightly curved downstream section 107 which terminates in an arcuate edge surface 109 which forms a major portion of the surface that abuts the valve sidewall, in the region downstream of the pivot axis in the closed position. The lateral edges of the occluder 103 are flat surfaces 111 which interconnect the major arcuate edge surface 109 and an upstream arcuate edge 113 which abuts the valve body sidewall upstream of the pivot axis when the occluder is in the closed position. The pivot arrangements are similar to those discussed hereinbefore, with lugs 115, 117 being formed in a pair of integral side sections 119 that flank the main flat body portion 105 of the occluder.

Figures 14, 15, 16:
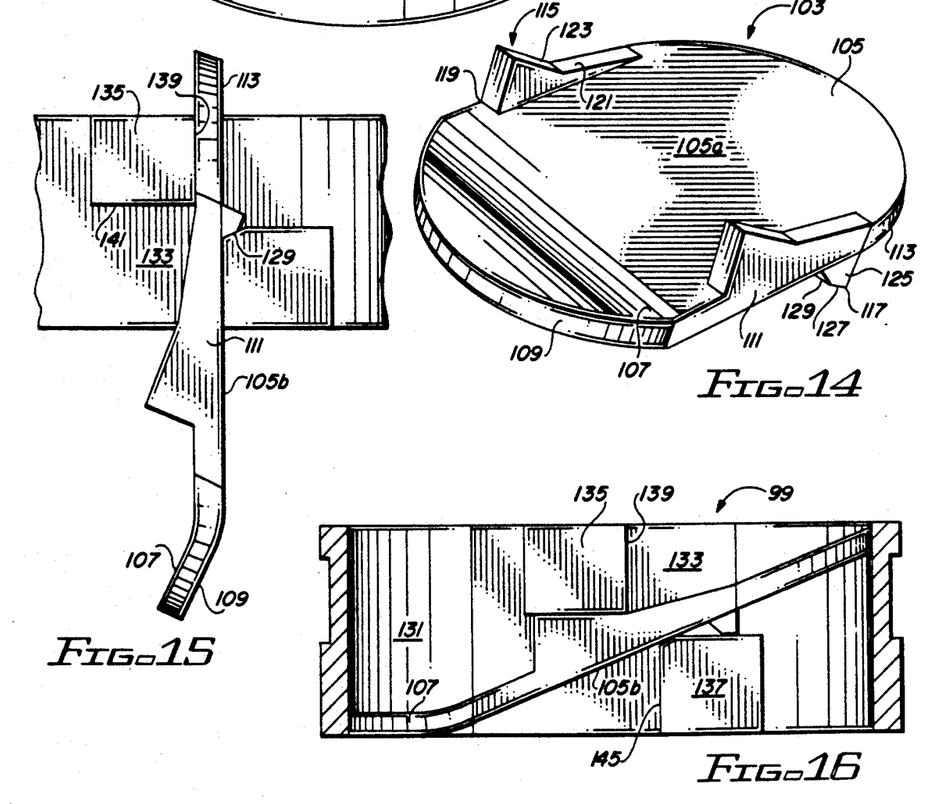
FIG. 14 is a perspective view of an occluder designed for use with the valve body of FIG. 13.
FIG. 15 is a fragmentary cross-sectional view of a heart valve utilizing the components of FIGS. 13 and 14 shown in the open position, with the occluder shown in elevation.
FIG. 16 is a cross-sectional view of the heart valve of FIG. 15 shown in the closed position.

The lugs 115 protrude from what is termed the inflow surface 105a of the occluder 103 and are sometimes referred to as the upstream or closing lugs because they extend in an upstream direction in the closed position as seen in FIG. 16. The lugs 115 have a front camming surface 121 which initiates the closing rotation and a rear surface 123 which is formed at an obtuse angle to the front camming surface 121. The downstream or opening lugs 117 extend from the outflow surface 105b of the occluder and in the illustrated embodiment are located entirely along the flat lateral edge surface 111. The lugs 117 are preferably slightly chamfered so as to have a slightly angularly oriented lateral surface 125 to provide clearance and avoid contact with the cylindrical sidewall of the valve body in the opening and closing movement. The lugs 117 each have a downstream surface 127 oriented to lie in juxtaposition with the transverse surface of the downstream projection of the valve body in the closed position. The lugs 117 also have an oblique surface 129 adjacent thereto which is oriented to engage and lie in juxtaposition with this downstream projection in the open position, as best seen in FIG. 15.

The valve body 101 is generally annular having a cylindrical sidewall surface 131 that is interrupted by a pair of diametrically opposed, flat sections 133. In the regions of the flat wall sections, there protrudes therefrom upstream projections 135 and downstream projections 137. The upstream projections 135 each have a flat sidewall 139 that is preferably parallel to the centerline through the valve body, and a downstream facing transverse surface 141 which may be perpendicular to the surface 139. The surfaces 139 and 141 meet along a downstream edge 143. The downstream projections 137 each have a flat surface 145 which is preferably parallel to the centerline plane of the valve and an upstream facing transverse surface 147, which is preferably perpendicular to the surface 145. In the illustrated embodiment, the surfaces 145 and 147 are interrupted by an intermediate oblique surface or facet 149 which is oriented at angle to the centerline of between about 30° and about 60°.

As illustrated in FIG. 15, when the occluder is in the open position, the oblique surface 129 is in contact with the intermediate surface 149 of the downstream projection 137, and the outflow surface 105b of the occluder lies in juxtaposition with the flat surface 145 of the downstream projection 137. A portion of the inflow surface 105a of the occluder also lies in juxtaposition with the flat surface 139 of the upstream projection 135.

In the closed position, as illustrated in FIG. 16, the rear surface 123 of each lug 115 lies in contact with the transverse surface 141 of the projection 135, and the arcuate edges 109, 113 are in contact with the cylindrical sidewall 131 of the valve body. The surface 127 of the lugs 117 lies in juxtaposition with the upstream facing transverse surface 147 of the downstream projection 137. In pivoting from the open to the closed surface 121 and the downstream edge 143 of the upstream projection, and there may be engagement between the outflow surface 105b of the occluder side sections and the edge between the surfaces 145 and 149 of the downstream projection. In other respects, the guidance of the rotational movement of the occluder is generally the same as hereinbefore described with respect to the leaflets.

Figure 17A:
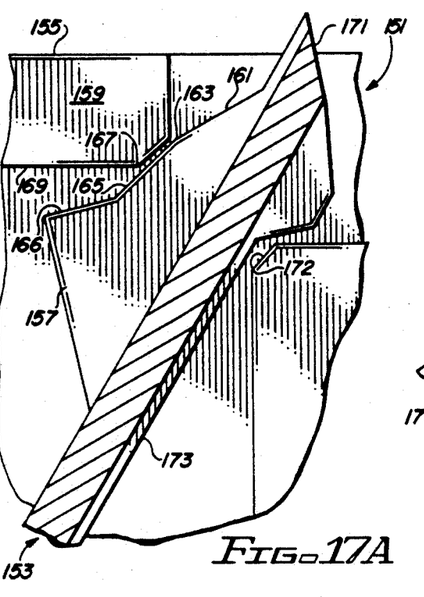
FIGS. 17A and B are cross-sectional views similar to FIGS. 7 and 9 showing another alternative embodiment of a heart valve having various features of the invention.
Figures 17B, 19:
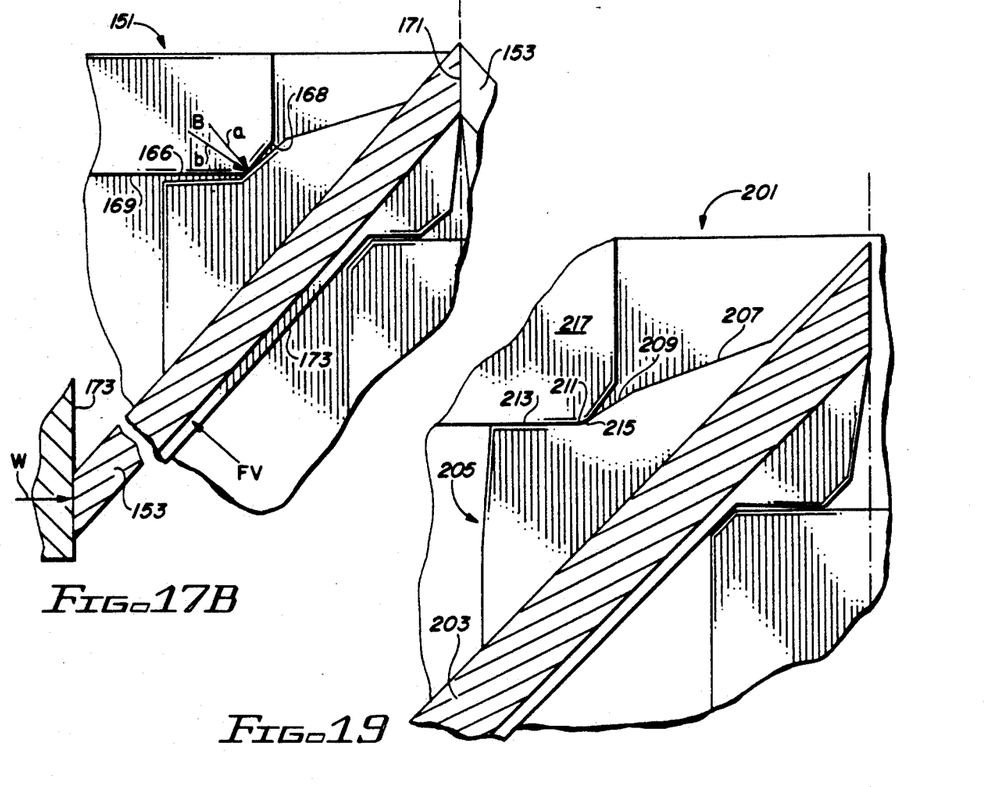
Figure 18:
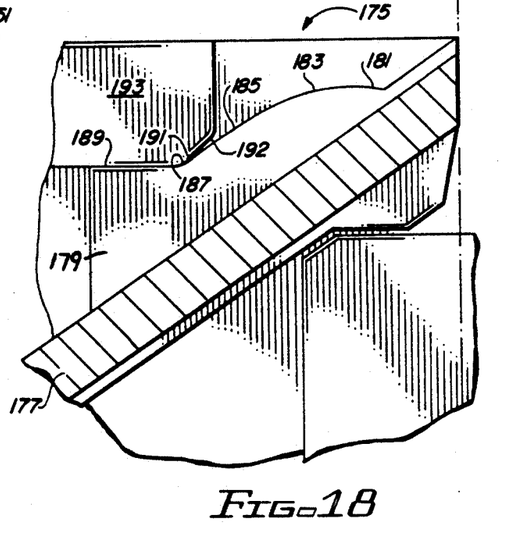
FIG. 18 is a cross-sectional view similar to FIG. 9 showing yet another alternative embodiment of a heart valve having various features of the invention.

Three alternative embodiments of bi-leaflet valves are shown in FIGS. 17-19. These are generally similar in most details to the bi-leaflet valve 10 described with respect to FIGS. 1 through 9. The main differences generally lie in the shaping of the projections that extend radially inward from the flat sidewall sections of the valve bodies and in the shaping of the lugs on the occluder side sections that interengage with these projections to guide the movement of the leaflets between their open and closed positions.

FIGS. 17A and B show a heart valve 151 having a pair of leaflets 153, which are mounted in an annular valve body 155 and which have upstream or closing lugs 157 that extend from the inflow surface of each leaflet or occluder and interengage with an upstream projection 159 during closing movement. The lugs 157 have camming surfaces made of different sections. More specifically, there is an initial camming ramp section 161 which is a surface oriented at an angle of about 27° to 29° to the centerline of the passageway (when the leaflet is in the open position). This section 161 leads to a central arcuate section 163, which in turn leads to a final shallow-inclined ramp section 165, which is a surface oriented at about 8° to 10° to the centerline plane of the valve (in the open position), before reaching the rear section 166.

The proportioning of these leaflets 153 is such and the location of the downstream edge 167 of the projections (at which edge an intermediate surface or facet 168 meets the transverse surface 169 and about which the final pivoting generally takes place) is such that there is a slight gap between the transverse surface 169 of the projection and the rear lug section 166 (that is located just to the rear of the final camming section 165 of the upstream lug). This arrangement allows a positive closing torque to be created about the downstream edge 167 (as indicated by the pair of arrows in FIG. 17B) which assures that the mating edges 171 of the two leaflets abut tightly in the closed position.

More specifically, at about the point of closure, the closing force is represented by the composite closing force vector FV, and the reaction forces are W (at the location where the arcuate edge of the leaflet bears against the cylindrical sidewall 173 of the valve body 155) and B, which is located at the point of engagement between the shallow camming surface 165 and the downstream edge 167 of the projection. If the orientation of the camming surface 165 was such that the force vector B was applied along the heavy dark line "a", these three forces would meet in a point (as illustrated with respect to the FIG. 2 embodiment), and there would be no positive closing torque. However, by orienting the final camming surface 165 so that the force vector B is offset by up to about 10° counterclockwise, as shown by the lighter arrow carrying the reference letter b, a positive torque is created which assures that the mating edges 171 of the two leaflets will tightly abut each other in the closed position. As seen in FIG. 17A and FIG. 17B, upstream facing facets 172 are provided on the downstream projections, oriented at an angle of between about 30° and about 60° (and preferably between about 45° and about 60°) to the valve centerline plane. These facets 172 lie in juxtaposition to the outflow surface extensions 173 of the opening lugs.

FIG. 18 shows a heart valve 175 which has a pair of leaflets 177 having some similarity to that just described with the FIG. 17 embodiment. More specifically, each leaflet has an upstream lug 179 formed with a first or front camming ramp 181 section that has a surface which is oriented at an angle of between about 25° and 30° which section leads to a fairly lengthy arcuate section 183, which in turn leads to a final flat section 185 that has a surface which is oriented parallel to the valve centerline plane (in the open position) and to the flat main body portion of the leaflet. There is also a curved transition region 187 at the junction between this parallel section 185 and the rear section 189 of the lug, and in the closed position (illustrated), the curved downstream edge 191 of an intermediate surface or facet 192 of the upstream projection 193 is received in this curved junction region 187 of the leaflet lug. In operation, the leaflets 177 function generally the same as the leaflets 14 shown and described in FIGS. 1 through 9. The closing rotation is instigated by the sliding engagement of the camming section 181 along the upstream projection intermediate facet or surface 192 and the edges thereof, with the continuation of the closing rotation being subsequently determined by the intermediate arcuate section 183 and the final parallel section 185.

FIG. 19 shows yet another heart valve 201 of bi-leaflet construction wherein each leaflet 203 has a pair of closing lugs 205 formed with two-section camming ramps, i.e. an initial section 207 that has a surface which is oriented at an angle of about 22° to 27°, leading to a second section 209 that has a surface which is oriented at an angle of about 10° to 12° (with respect to the valve centerline plane in the open position). This second section leads to a concave-curved surface 211 which forms the transition to the rear surface 213 of the lug, and the curvature of this surface is carefully matched so as to be substantially the same as the radius of curvature of the downstream edge 215 of the projection 217. As a result, in the closed position, the downstream edge 215 is received in this concave-curved region between the flat rear surface 213 and the second camming surface section 209, and a stable arrangement is achieved.

Although the invention has been described with respect to a number of preferred embodiments, which include the best mode presently understood by the inventor for carrying out the invention, it should be understood that various changes and modifications as would be obvious to one having the ordinary skill in this art may be made without departing from the scope of the invention which is defined by the claims appended hereto.

Particular features of the invention are emphasized in the claims that follow.

What is claimed is:

1. A prosthetic heart valve which comprises
   a generally annular valve body having an interior sidewall which defines a central passageway therethrough, for passage of blood flow in a downstream direction, having a centerline extending in a direction of blood flow,
   occluder means having a curved inflow surface and a curved outflow surface which is mounted in said valve body to alternately permit the flow of blood therethrough in a downstream direction when in an open position and block the flow of blood in a reverse direction when in a closed position,
   said valve body and said occluder means having a pivot arrangement by which said occluder means is guided in moving between said open position and said closed position,
   said pivot arrangement including at least one pair of first and second projections extending inward from said valve body sidewall and including first and second lug means on said occluder means for engaging said projections, said lug means protruding respectively in opposite directions,
   each of said projections being formed with flat first surfaces oriented substantially parallel to the centerline of said central passageway and each of said projections also having a second surface that is oriented generally transversely to said first surface, and
   said projections being positioned so that, when said occluder means is in the open position, oppositely facing surfaces on said occluder means respectively lie in juxtaposition with said first surfaces of said projections and said first lug means engages said first projection in a general region of said second surface.

2. A prosthetic heart valve according to claim 1 wherein said occluder means is formed with a main body section in a shape of a section of a hollow cylinder which provides said curved inflow surface and said curved outflow surface and also with a pair of flanking side sections, said first and second lug means being formed in said flanking side sections.

3. A prosthetic heart valve according to claim 2 wherein said occluder main body section is aligned in the open position so that an axis of said hollow cylinder and said curved inflow and outflow surfaces are aligned substantially parallel to said central passageway centerline.

4. A prosthetic heart valve according to claim 1 wherein said second surface of said first projection which is engaged by said first lug means in said open position faces generally upstream and wherein, upon reversal of flow of blood through said valve body, said occluder means is displaced upstream with said second lug means engaging said second projection and causing said occluder means to promptly begin to rotate toward a closed position orientation.

5. A prosthetic heart valve according to claim 1 wherein said valve body includes two pairs of first and second projections at generally diametrically opposite locations, said projections of each pair being spaced from each other so that lateral edge portions of said occluder means are received therebetween.

6. A prosthetic heart valve according to claim 5 wherein said second lug means extends in a direction generally away from said inflow surface of said occluder means and contains a first upstream surface oriented at an angle of between about 5° and about 35° to a plane containing said valve centerline when said occluder means is in the open position and wherein said second surfaces of said second projections are located upstream of said second surfaces of said first projections.

7. A prosthetic heart valve according to claim 6 wherein said second surfaces of said second projections are substantially perpendicular to said first surface thereof and wherein each said second lug means has a second upstream surface which is oriented at an angle of between about 30° and about 45° to the centerline of said central passageway when said occluder means is in the open position and which generally abuts said second surface of said second projection when said occluder means is in said closed position.

8. A prosthetic heart valve which comprises
   a generally annular valve body having an interior, generally arcuate sidewall which defines a central passageway therethrough, for passage of blood flow in a downstream direction, having a centerline extending in a direction of blood flow,
   a pair of cooperating occluders, each having a curved inflow surface and a curved outflow surface which are mounted in said valve body to alternately permit the flow of blood therethrough in a downstream direction when in an open position and block the flow of blood in a reverse direction when in a closed position,
   said valve body and said occluders having a pivot arrangement by which said occluders are guided in moving between said open position and said closed position,
   said pivot arrangement including first and second projection means extending inward from said valve body sidewall and including first and second lug means protruding in opposite directions from each said occluder for engaging said projection means,
   each of said projection means being formed with flat first surfaces oriented substantially parallel to the centerline of said central passageway and each said projection means also having a second surface that is oriented generally transversely to said first surface, said second projection means including a separate second projection separate from each of said first projection means, and
   said first and second projection means being positioned so that, when each said occluder is in the open position, portions of each said occluder lie in juxtaposition with said first surfaces of said first and second projection means and said first lug means of each occluder engages said first projection means.

9. A prosthetic heart valve according to claim 8 wherein each occluder is formed with a main body section in a form of a section of a hollow cylinder which provides said curved inflow surface and said curved outflow surface and with a pair of flanking side sections, said first lug means and said second lug means being formed in said flanking side sections.

10. A prosthetic heart valve according to claim 9 wherein said first lug means in said open position engages said second surface of said first projection means which surface faces generally upstream and wherein, upon reversal of flow of blood through said valve body, each said occluder is displaced upstream so that said second lug means of each occluder engages one of said second projections causing said occluder to promptly begin to rotate toward a closed position orientation.

11. A prosthetic heart valve according to claim 10 wherein said valve body includes a set of said first and second projection means at each of two generally diametrically opposite locations, said second projections of each said set being located in upstream position with respect to said first projection means and having second surfaces which are substantially perpendicular to said centerline, said first and second projection means of each said set being spaced from one another so that said flanking side sections of said occluders are received therebetween.

12. A prosthetic heart valve which comprises
a generally annular valve body having an arcuate interior sidewall which is interrupted by a pair of generally diametrically opposed flat sections and which defines a central passageway therethrough, for blood flow in a downstream direction, having a centerline which extends parallel to blood flow,
occluder means having a curved inflow surface and a curved outflow surface which is mounted in said valve body to alternately permit the flow of blood therethrough in a downstream direction when in an open position and block the flow of blood in a reverse direction when in a closed position,
said valve body and said occluder means having a pivot arrangement by which said occluder means is guided in moving between said open position and said closed position,
said pivot arrangement including projections which extend inward from said flat sections of said valve body sidewall and lug means formed upon a surface of said occluder means for camming contact with said projections, said lug means having front and rear sections,
said projections being positioned so that, when said occluder means is in the open position, portions of inflow and outflow surfaces of said occluder means lie in juxtaposition with surfaces of said projections,
said occluder means and said valve body having interengaging means which limit further downstream movement of said occluder means in the open position, and
said positioning of said projections being such that upstream displacement of said occluder means upon reverse of direction flow of blood causes rotational movement to promptly occur as said occluder means begins to move from the open position to the closed position, which rotational movement is initially at least partially defined by sliding engagement between said front sections of said lug means and said projections and is subsequently at least partially defined by engagement between said projections and said rear sections of said lug means.

13. A prosthetic heart valve according to claim 12 wherein said occluder means is formed with a main body section of substantially uniform thickness and a pair of flanking side sections with said lug means being formed in said flanking side sections.

14. A prosthetic heart valve according to claim 13 wherein said flanking side sections also are formed with ears which protrude in generally diametrically opposite directions, said occluder means being proportioned so that ears from only one side section engage said valve body arcuate sidewall at a time as said occluder means rotates toward the closed position.

15. A prosthetic heart valve according to claim 12 wherein said valve body includes other projections at each of said flat sidewall sections, said other projections being respectively spaced from said projections so that a lateral edge of said occluder means is received therefrom, wherein said front section of each said lug means is inclined at an angle of between about 5° and about 35° to said centerline with reference to said occluder means is in the open position, and wherein other lug means projecting from said occluder means and facing in opposite directions from said lug means interengage with said other projections, constituting said interengaging means which limits further downstream movement in the open position.

16. A prosthetic heart valve which comprises
a generally annular valve body having an interior sidewall which defines a central passageway therethrough, for passage of blood flow in a downstream direction, having a centerline which extends in parallel to a direction of blood flow,
a pair of occluders each having a curved inflow surface, a curved outflow surface, a mating edge surface and an arcuate downstream edge surface, said occluders being mounted in said valve body to permit the flow of blood therethrough in a downstream direction when in an open position with said mating edges spaced apart from each other and to alternately block the flow of blood in a reverse direction when in a closed position with said mating edge surfaces abutting each other, said curved inflow and outflow surfaces being rectilinear surfaces made up of parallel lines from said mating edge surface to said arcuate downstream edge surface and which can be parallel to said passageway centerline in the open position,
said valve body and said occluders having a pivot arrangement by which said occluders are guided in moving between said open position and said closed position, with said valve body having projection means extending inward from said interior sidewall,
each said occluder being formed with a flat camming region generally along said inflow surface located for engaging said projection means so as to guide said occluder in pivoting to the closed position,
said projection means being so positioned and said flat camming regions on said inflow surfaces being so inclined that, when each occluder arcuate downstream edge contacts said valve body interior sidewall in its movement toward its closed position, forces acting upon each said occluder are so aligned that, as a result, there is a small composite force acting upon said occluder which tends to cause said mating edges to rotate into contact with each other.

17. A heart valve according to claim 16 wherein each occluder has a tubular main body section of substantially uniform thickness on which said curved inflow and outflow surfaces are formed.

18. A heart valve according to claim 17 wherein said inclined flat camming regions of said occluders have surfaces which are oriented at an angle of between about 30° and about 5° to a plane containing the centerline of said valve body when said occluders are in the open position.

19. A heart valve according to claim 17 wherein each said occluder has a length such that, when its arcuate downstream edge contacts said valve body sidewall, the mating edge surface thereof extends just slightly past the valve centerline.

20. A prosthetic heart valve which comprises
   a generally annular valve body having an arcuate interior sidewall which is interrupted by a pair of generally diametrically opposed flat sections and which defines a central passageway therethrough, for blood flow in a downstream direction, having a centerline which extends parallel to blood flow,
   occluder means having a curved inflow surface and a curved outflow surface which is mounted in said valve body to alternately permit the flow of blood therethrough in a downstream direction when in an open position and block the flow of blood in a reverse direction when in a closed position,
   said valve body and said occluder means having a pivot arrangement by which said occluder means is guided in moving between said open position and said closed position,
   said occluder means is formed with a main body section and with a pair of flanking side sections,
   said pivot arrangement includes projections which extend inward from said flat sections of said valve body sidewall and includes lug means formed in each of said flanking side sections for camming contact with said projections, said lug means having front and rear sections,
   said projections being positioned so that, when said occluder means is in the open position, portions of surfaces of said occluder means lie in juxtaposition with surfaces of said projections,
   said occluder means flanking side sections and said valve body also have interengaging means which limit further downstream movement of said occluder means in the open position,
   said positioning of said projections is such that upstream displacement of said occluder means upon reverse direction flow of blood causes rotational movement to promptly occur as said occluder means begins to move from its open position to its closed position, which rotational movement is initially at least partially defined by sliding engagement between said front sections of said lug means and said projections and thereafter is at least partially defined by engagement between said projections and said rear sections of said lug means, and
   said occluder means flanking side sections are also formed with ears which protrude in generally diametrically opposite directions, said occluder means being proportioned so that an ear of only one of said flanking side sections at a time engages said valve body arcuate sidewall and thereby partially defines a path of movement of said occluder means toward the closed position.

* * * * *

UNITED STATES PATENT AND TRADEMARK OFFICE
CERTIFICATE OF CORRECTION

PATENT NO. : 5,246,453
DATED : September 21, 1993
INVENTOR(S) : Bokros, et al

It is certified that error appears in the above-indentified patent and that said Letters Patent is hereby corrected as shown below:

Column 9, line 44, after "interengage" insert --with the recesses 56a, and the downstream-facing surfaces 56--.

Column 13, line 16, after "closed" insert --position, there is sliding engagement between the camming--.

Claim 6, column 16, line 4, after "wherein" insert --each--.

Claim 8, column 16, line 51, change "separate" (first occurence) to --spaced--.

Claim 9, column 16, line 61, after "of" insert --the--.

Claim 12, column 17, line 54, after "reverse" delete "of".

Claim 13, column 17, line 65, after "a" insert --curved--.

Claim 15, column 18, lines 12-13, change "therefrom" to --therebetween--.

Claim 15, column 18, lines 15-16, after "means" delete "is".

Claim 16, column 18, line 27, after "extends" delete "in".

Signed and Sealed this

Tenth Day of May, 1994

Attest:

BRUCE LEHMAN

Attesting Officer

Commissioner of Patents and Trademarks